US00PP35206P3

(12) United States Plant Patent
Ruter

(10) Patent No.: US PP35,206 P3
(45) Date of Patent: Jun. 6, 2023

(54) ***THUJA* PLANT NAMED 'RUTTHU3'**

(50) Latin Name: *Thuja occidentalis*
Varietal Denomination: RutThu3

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/854,193

(22) Filed: Jun. 30, 2022

(65) Prior Publication Data

US 2023/0007821 P1 Jan. 5, 2023

Related U.S. Application Data

(60) Provisional application No. 63/217,004, filed on Jun. 30, 2021.

(51) Int. Cl.
*A01H 7/00* (2006.01)

(52) U.S. Cl.
USPC ..... Plt./213

CPC ..... *A01H 7/00* (2013.01)

(58) Field of Classification Search
USPC ..... Plt./213
See application file for complete search history.

(56) References Cited

PUBLICATIONS https://firsteditionsplants.com/product/lemon-burst-arborvitae/.*
https://tmsearch.uspto.gov/bin/showfield?f=doc&state=4810:mh5ytx.3.8.*
https://inspection.canada.ca/english/plaveg/pbrpov/cropreport/ced/app00012408e.shtml.*

* cited by examiner

*Primary Examiner* — Susan McCormick Ewoldt
(74) *Attorney, Agent, or Firm* — Thomas Horstemeyer, LLP

(57) ABSTRACT

A new and distinct cultivar of *Thuja* plant named 'RutThu3', characterized by its compact, rounding form and yellow foliage with orange tips; growth and heat tolerance in USDA Zone 8a, growth in full sun and afternoon shade conditions in landscape and full sun in container production, disease and insect resistance, and cold hardiness to about −34° F. in Minnesota.

2 Drawing Sheets

Figure 1:
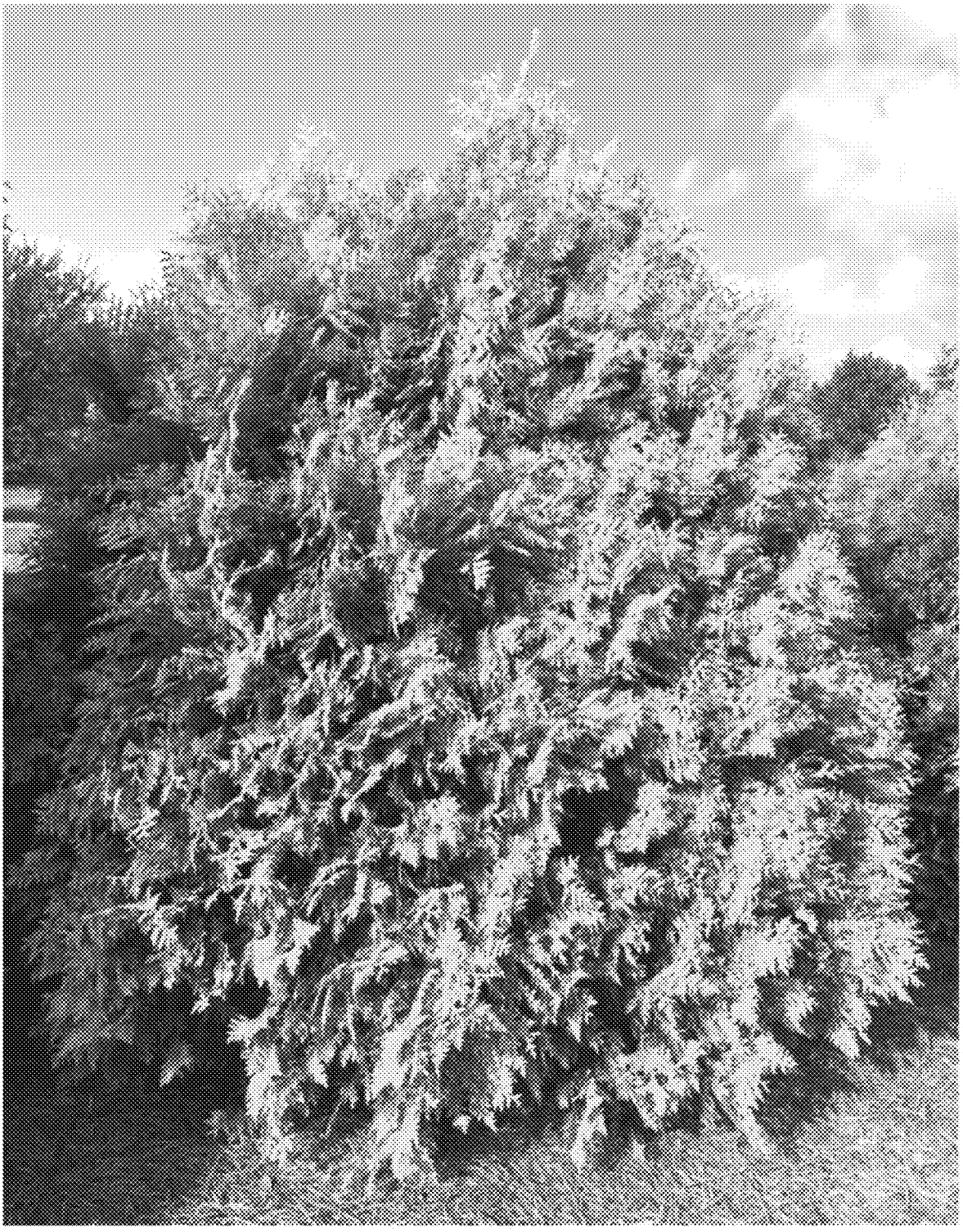

Botanical designation: *Thuja occidentalis.*
Cultivar denomination 'RutThu3'.

BACKGROUND OF THE INVENTION

The present invention relates to a new and distinct cultivar of *Thuja*, botanically know as *Thuja occidentalis*, and hereinafter referred to by the cultivar name 'RutThu3'.

The new *Thuja* cultivar 'RutThu3' is a product of open pollination of *Thuja occidentalis* 'Albo-spicata' (unpatented female parent). The open-pollinated seeds were obtained from Latvia in 2013. Seedlings were planted in Watkinsville, Ga. in 2015. The new cultivar 'RutThu3' was selected for its compact, rounded form, yellow foliage with orange-toned tips, growth in full sun or afternoon shade, and cold hardiness to about −34° F. in trials conducted in Minnesota.

Asexual reproduction of the new *Thuja* 'RutThu3' using hardwood cuttings was first conducted in Watkinsville, Ga. in 2015 and has been continued in Watkinsville, Ga. since. Observations of the resulting progeny have shown that the unique features of this new *Thuja* 'RutThu3' are stable and reproduced true to type in successive generations. The new 'RutThu3' has also been grown in Minnesota.

SUMMARY OF THE INVENTION

The new *Thuja* cultivar 'RutThu3' has not been observed under all possible environmental conditions. The phenotypes may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Thuja* cultivar named 'RutThu3'. In combination, these traits set 'RutThu3' apart from all other existing varieties of *Thuja* known to the inventors.

1. Compact, rounded growth form, compared to the more oval shape of other *Thuja occidentalis* cultivars, such as 'Yellow Ribbon' (unpatented);
2. yellow foliage with orange-toned tips;
3. grows and thrives in USDA zone 8a with superior heat tolerance to other yellow-foliaged cultivars and no summer foliage burning;
4. growth in full sun or part-shade in the landscape;
5. growth in full sun in container production;
6. cold hardy to about −34° F. in trials conducted in Minnesota Plants of the 'RutThu3' can be compared to similar yellow-foliaged cultivar *Thuja occidentalis* 'Yellow Ribbon' (unpatented) and differs from 'Yellow Ribbon' in that 'RutThu3' has a compact, rounded shape as opposed to oval. 'Yellow Ribbon' has a size (h×w) of about 91"×76" (ratio about 1.2) compared to the more rounded size/shape of 'RutThu3' at about 72"×72" (ratio about 1.0) 'RutThu3' has superior heat tolerance to 'Yellow Ribbon' and other yellow-foliaged cultivars that grow in USDA Zone 8a.

The new 'RutThu3' can also be compared to maternal parent *Thuja occidentalis* 'Albo-spicata', which has splatterings of white tissue on new growth as opposed to the new growth of 'RutThu3', which has orange-toned tips. Final size and growth rate are similar to female parent. Male parent plant is not conclusively known, so comparison data is not available.

BRIEF DESCRIPTION OF THE PHOTOGRAPHS

The accompanying, colored photographic illustrations show the overall appearance and distinct characteristics of the new cultivar *Thuja* 'RutThu3' showing the colors as true as possible. Colors in the photographs may differ slightly from the color values cited in the detailed botanical description. The photographs were taken around June, 2021 on plants grown outdoors in Watkinsville, Ga.

The photograph labeled FIG. 1 depicts a side view of a typical 9-year-old 'RutThu3' plant showing the compact, rounded form and features and yellow toned foliage.

Figure 2:
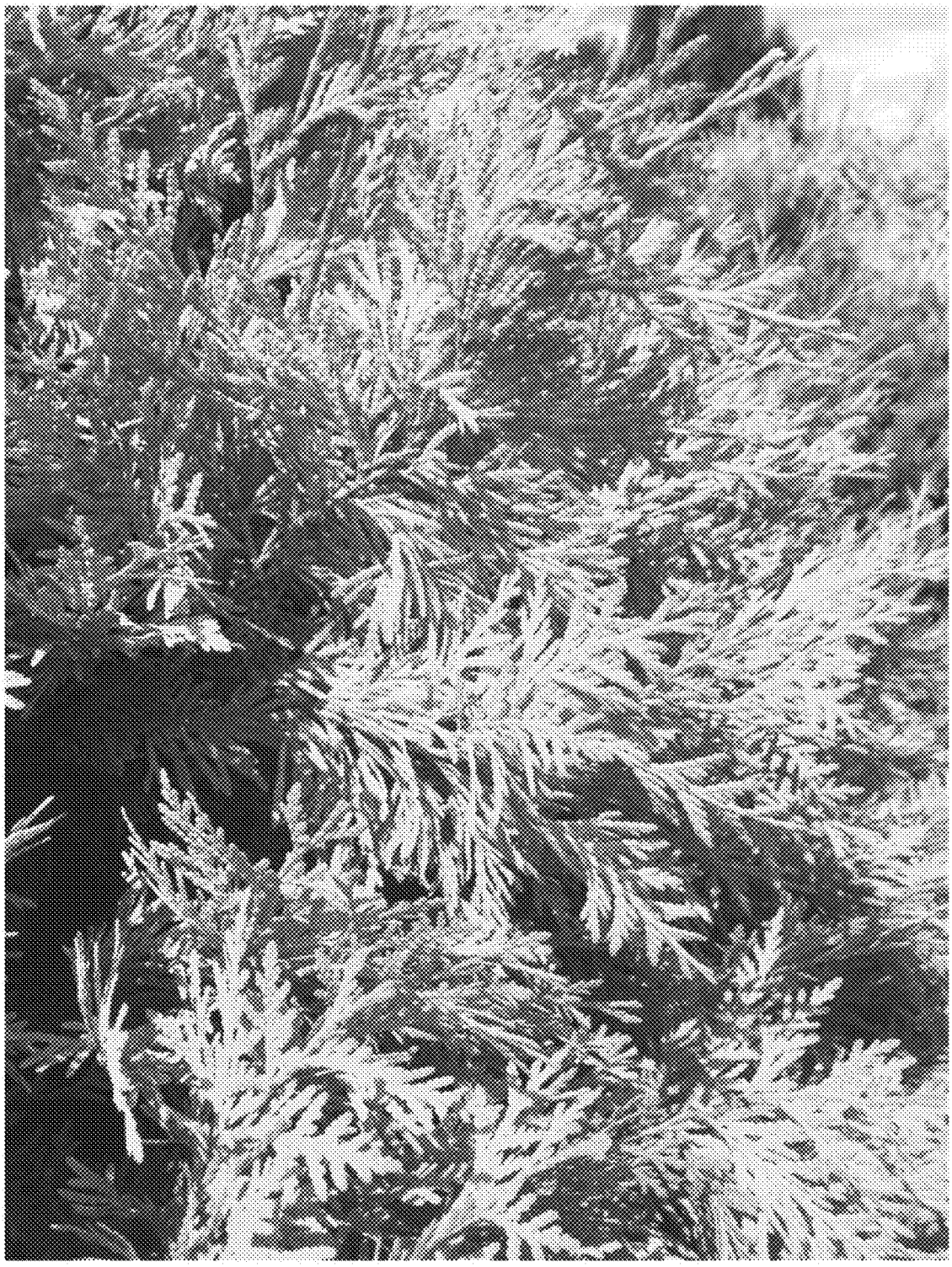

The photograph labeled FIG. 2 depicts a close-up view of the branches and needles of a typical 9-year-old 'RutThu3' plant showing the yellow-colored foliage and the orange-toned tips of new growth.

DETAILED BOTANICAL DESCRIPTION

The following traits have been consistently observed in the original plants of the new varieties and in asexually propagated progeny grown in Watkinsville, Ga., (and some in Minnesota) and, to the best knowledge of the inventors, their combination forms the unique characteristics of the new variety 'RutThu3'.

Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society, London, England in 2007, except where general terms of ordinary dictionary significance are used.

The aforementioned photographs and following observations, measurements, and values describe plants of the *Thuja* cultivar named 'RutThu3'. Data were collected from a horticulture farm and nursery in Watkinsville, Ga. from 8-year-old plants. The average low temperatures ranged from about 20° F. to 30° F. in the winter and about 90° F. to 100° F. in summer.

Botanical classification: *Thuja* 'RutThu3'.

Commercial classification: Ornamental conifer.

Parentage: Open pollination of mixed *Thuja occidentalis* 'Albo-spicata' by unknown pollen parents.

Growth and propagation:

*Propagation type.*—Terminal or sub-terminal hardwood cuttings.

*Root description.*—Typically about 2-5 roots arising from the base of the cuttings.

*Rooting habit.*—Moderate.

Plant description:

*Habit.*—Of 6-year-old plant in field — Compact, rounded.

*Usage.*—Various uses, including landscaping, ornamental, container, border, hedge, and mass planting.

*Vigor.*—Moderate.

*Size of 6-year-old plant.*—A. Height: from soil level to top of plant, about 72 inches. B. Width: about 72 inches. C. Ratio: about 1.0.

*Trunk bark.*—A. Texture: smooth, semi-gloss. B. Color: Grey-Orange 177B.

*Branch/stem (terminal tuft).*—A. Quantity: numerous with an average of about 11-13 branches/stems per linear foot of main stem. B. Length: (of year 1 stem) about 15 cm. C. Base Diameter: (of second year stem) about 3-4 mm at 15 cm from tip. D. Branch angle: about 45° from center. E: Odor (of bruised stem): mild evergreen. F. Internode length: about 2-2.5 cm. G: Color (R.H.S.): (½ year stem) Yellow green 155A to Greyed orange 177C. H: Strength of lateral branches: strong. I: Pubescence: none. J: Shape: round.

*Leaf.*—A. Leaf type: scale. B. Mature size (L×W): about 3 mm×about 2 mm. C. Arrangement on stem: decussate. D. Aspect: upright. E. Color (R.H.S.) — upper — Yellow 7A. lower — Yellow 8B. tips — Yellow orange 17A. F. Leaf Number: average of about 12 per cm/stem. G. Apex: acute-acuminate. H. Base: rounded. I. Margin: Smooth/Hyaline. J. Shape: scale; lobes absent. K. Pubescence: none. L. Venation: none. M. Texture: waxy with abaxial gland. O. Odor when crushed: mild evergreen.

*Long shoots.*—A. Facial Gland: present. B. Leaf Shape: scale. C. Color: Greyed orange 177C. D. Tips: free and appressed tips. E. Apex: acute.

*Coning production.*—None.

*Seed.*—None.

Weather/temperature tolerance: Plants of the new *Thuja* have heat tolerance in USDA Zone 8a, with better heat tolerance than similar yellow-foliaged *Thuja* cultivars, and have a USDA Zone range 3-9. 'RutThu3' thrives in full sun and afternoon shade in landscape and full sun for container production. The new 'RutThu3' has also demonstrated cold hardiness to about −34° F. in trials conducted in Minnesota.

Disease/pest resistance: To date, plants of the new *Thuja* have not shown any disease or insect issues in field and container trials.

It is claimed:

1. A new and distinct cultivar of the *Thuja* plant named 'RutThu3' as illustrated and described herein.

* * * * *